United States Patent [19]
Lee et al.

[11] Patent Number: 6,150,560
[45] Date of Patent: Nov. 21, 2000

[54] RECOVERY OF TRIS(ARYL)BORANE FROM THEIR TETRAHYDROFURAN COMPLEXES

[75] Inventors: John Y. Lee; Jamie R. Strickler, both of Baton Rouge, La.

[73] Assignee: Albemarle Corporation, Richmond, Va.

[21] Appl. No.: 09/299,554

[22] Filed: Apr. 22, 1999

[51] Int. Cl.$^7$ ........................................ C07F 5/02
[52] U.S. Cl. ............................................ 568/6; 568/1
[58] Field of Search ................................. 568/1, 6

[56] References Cited

U.S. PATENT DOCUMENTS

| | | | |
|---|---|---|---|
| 5,510,536 | 4/1996 | Ikeda et al. | 568/6 |
| 5,545,759 | 8/1996 | Ikeda et al. | 568/6 |
| 5,600,004 | 2/1997 | Diefenbach | 568/1 |
| 5,693,261 | 12/1997 | Krzystowczyk et al. | 260/665 G |
| 5,959,151 | 9/1999 | Lee et al. | 568/1 |

FOREIGN PATENT DOCUMENTS 0838466  4/1998  European Pat. Off. .

OTHER PUBLICATIONS

Horsley, Lee L., "Azeotropic Data–III", Am. Chem. Soc., Advances In Chemistry Series 116, 1973, pp. 227 and 251.

*Primary Examiner*—Jean F Vollano
*Attorney, Agent, or Firm*—Philip M. Pippenger

[57] ABSTRACT

This invention relates to methods for separating tris(aryl) boranes from tris(aryl)boranetetrahydrofuran complexes in hydrocarbon solvents via distillation.

23 Claims, No Drawings

RECOVERY OF TRIS(ARYL)BORANE FROM THEIR TETRAHYDROFURAN COMPLEXES

TECHNICAL FIELD

This invention relates to methods for separating tris(aryl) boranes from their tris(aryl)boranetetrahydrofuran complexes in hydrocarbon solvents.

BACKGROUND

Methods for dissociating tris(aryl)boraneether complexes are well known. These methods include evaporation of the ether with sublimation; reactive exchange, in which a compound that has a higher affinity for the ether is added; and azeotropic distillation from a higher-boiling hydrocarbon solvent. Some of these methods are described in U.S. Pat. Nos. 5,510,536, 5,600,004, 5,693,261, and EP 838466A2. However, the tris(aryl)boraneether complexes formed when tetrahydrofuran is the ether are especially strong and difficult to separate. A satisfactory yield of the separated tris(aryl) borane is often not obtained by azeotropic distillation when tetahydrofuran is the complexed ether. Thus, there remains a need for a method which more completely separates tris(aryl)boranes from tetrahydrofuran.

THE INVENTION

This invention makes possible a more complete separation of tris(aryl)boranes and tetrahydrofuran from tris(aryl) boranetetrahydrofuran complexes. In fact, this invention enables essentially complete dissociation of the tetrahydrofuran complex and essentially complete separation of the liberated tetrahydrofuran from the tris(aryl)borane. Pursuant to this invention, a distillation is performed in a non-complexing solvent and under special temperature conditions. Thus, an embodiment of this invention involves a process for removal of tetrahydrofuran from a tris(aryl) boranetetrahydrofuran complex, which process comprises nonazeotropically distilling tetahydrofuran at a temperature in the range of from about 115° C. to about 160° C. from a mixture comprising an inert hydrocarbon solvent composition and a tris(aryl)boranetetrahydrofuran complex.

In one preferred embodiment, excellent results can be achieved using as the solvent a mixture of paraffinic hydrocarbons boiling in the range of from about 114° C. to about 126° C. In this embodiment, the operation can be conducted either at atmospheric pressure or at superatmospheric pressures.

In another preferred embodiment, the solvent used is toluene, and the operation is conducted at an elevated pressure sufficient to maintain the solvent in the liquid state.

Further embodiments of this invention will be apparent from the ensuing description and appended claims.

The aryl groups of the tris(aryl)borane may be the same or different; it is preferred that all three aryl groups are the same. The aryl moiety may be phenyl, biphenylyl, naphthyl, anthracenyl, phenanthrenyl, naphthacenyl, chrysenyl, perylenyl, terphenyl, binaphthyl, and the like. Most preferred as the aryl moiety is a phenyl group. The aryl groups may be substituted by one or more fluorine atoms, hydrocarbyl groups, alkoxy groups, and/or perfluorinated hydrocarbyl groups.

The hydrocarbyl group substituents are preferably $C_6$ to $C_{24}$ aryl groups or $C_1$ to $C_{10}$ alkyl groups. Examples of suitable hydrocarbyl groups are methyl, ethyl, isopropyl, tert-butyl, cyclopentyl, methylcyclohexyl, decyl, phenyl, tolyl, xylyl, and naphthyl. The alkoxy groups preferably have $C_1$ to $C_6$ alkyl moieties. Some examples of alkoxy groups are methoxy, ethoxy, propoxy, isopropoxy, methylcyclopentoxy, and cyclohexoxy. The perfluorinated hydrocarbyl groups include alkyl and aryl perfluorocarbons; suitable perfluorinated hydrocarbyl groups are, for example, trifluoromethyl, pentafluoroethyl, pentafluorophenyl, and heptafluoronaphthyl.

It is preferred that at most two substituents on the aryl ring are hydrocarbyl, perfluorinated hydrocarbyl, or alkoxy, while the rest of the substituents are fluorine atoms. It is highly preferred to have aryl rings in which the all of the substituents are fluorine atoms. Examples of such groups are pentafluorophenyl, nonafluorobiphenylyl, heptafluoronaphthyl, nonafluoroanthracenyl, nonafluorophenanthrenyl, undecafluoronaphthacenyl, undecafluorochrysenyl, undecafluoroperylenyl, tridecafluoroterphenyl, tridecafluorobinaphthyl, and the like. Most preferred as the aryl group is a pentafluorophenyl group; thus, the most highly preferred tris(aryl)borane is tris(pentafluorophenyl)borane.

The hydrocarbon solvent composition may be made up of a mixture of hydrocarbons such that a liquid mixture is formed; all of the components of the hydrocarbon solvent composition should be inert towards the tris (pentafluorophenyl)borane. Linear, branched, and/or cyclic saturated hydrocarbons and/or linear, branched, and/or cyclic nonaromatic unsaturated hydrocarbons may be used to make the mixture. The hydrocarbon solvent composition may instead be made up of aromatic hydrocarbons; such a mixture should also be a liquid.

Some examples of saturated hydrocarbons that may be used in forming a hydrocarbon solvent composition are pentane, cyclohexane, methylcyclohexane, ethylcyclooctane, decane, 6-propyldodecane, and eicosane. Examples of nonaromatic unsaturated hydrocarbons that may be used in forming a hydrocarbon solvent composition include cyclopentene, 1-hexene, 2,5-dodecene, and 1,4-cyclooctadiene. Mixtures of saturated hydrocarbons are a preferred hydrocarbon solvent composition; more preferred are mixtures of saturated hydrocarbons that are structural isomers. A highly preferred hydrocarbon solvent composition is Isopar-E, a product of Exxon, which is a mixture of paraffinic $C_8$ hydrocarbons with a boiling point range of 114° C. to 126° C. Some examples of aromatic hydrocarbons that may be used in forming a hydrocarbon solvent composition are toluene, ethylbenzene, isopropylbenzene, xylene, ethylmethylbenzene, diethylbenzene, methylisopropylbenzene, and mesitylene. The use of a single aromatic hydrocarbon is also a preferred hydrocarbon solvent composition; toluene is a highly preferred aromatic hydrocarbon for the hydrocarbon solvent composition. The foregoing solvents which may make up the hydrocarbon solvent composition do not form azeotropes with tetrahydrofuran in the distillation temperature range of from about 115° C. to about 160° C.

When the tris(aryl)boranetetrahydrofuran complex is from a crude reaction mixture, it will probably contain side products from its formation, such as magnesium salts; these side products usually precipitate as tetrahydrofuran is driven off. Mixing a large amount of tris(aryl) boranetetrahydrofuran complex from a crude reaction mixture with the hydrocarbon solvent composition is generally undesirable because an intractable amount of solid precipitate can form. Preferably, the tris(aryl) boranetetrahydrofuran complex may be up to about fifteen weight percent of the mixture, but is more preferably less than ten weight percent, and most preferably less than six weight percent of the mixture.

While it is possible to add the hydrocarbon solvent composition to the tris(aryl)boranetetrahydrofuran complex, it is preferred that the tris(aryl)boranetetrahydrofuran complex be added to the hydrocarbon solvent composition, and it is more preferred that the hydrocarbon solvent composition is already at an elevated temperature when the tris(aryl)boranetetrahydrofuran complex is added. It is advantageous to add the tris(aryl)boranetetrahydrofuran complex to hydrocarbon solvent composition at an elevated temperature because any precipitate that forms tends to be a fine particulate rather than a clumpy solid. Further, the elevated temperature allows the removal of any uncomplexed tetrahydrofuran that may be present. The elevated temperature is preferably at least about 70° C., but less than about 115° C.

After mixing the tris(aryl)boranetetrahydrofuran complex and the hydrocarbon solvent composition, the temperature of the mixture is raised to at least about 115° C., and preferably to at least about 120° C. It is highly preferred to heat the mixture to a temperature in the range of from about 120° C. to about 140° C. The temperature should not exceed about 160° C., as the tris(aryl)borane tends to slowly undergo thermal decomposition at or above this temperature. At temperatures above 160° C., the thermal decomposition is accelerated in the presence of noninert impuritites. When the hydrocarbon solvent composition has a boiling point less than about 115° C., increased pressure is generally necessary for the distillation to occur in the desired temperature range. Distillation under increased pressure is preferably conducted at pressures up to about 40 psig; more preferred are pressures in the range of from about 0.5 psig to about 30 psig. It may be necessary in the course of the invention to vary from the pressures described herein to attain the desired distillation temperature, as deemed necessary by those skilled in the art.

When the temperature at which the tetrahydrofuran is removed is above the lower temperature of the boiling range of the hydrocarbon solvent composition, it is often necessary to replace some of the hydrocarbon solvent composition during the tetrahydrofuran distillation. Typical amounts of replacement hydrocarbon solvent composition are in the range of from about 1.0 to about 4.0 times the initial amount of hydrocarbon solvent composition used. It is preferred to conduct the tetrahydrofuran distillation in a hydrocarbon solvent composition that is boiling.

The following examples are presented for purposes of illustration, and are not intended to impose limitations on the scope of this invention.

EXAMPLE 1

Tris(pentafluorophenyl)boranetetrahydrofuran, made by mixing 1.0 g of solid tris(pentafluorophenyl)borane in 2.0 g of dry tetrahydrofuran, is added slowly under nitrogen to 45.0 g of Isopar-E at 110° C. to 118° C. Isopar-E is a product of Exxon, which is a mixture of paraffinic $C_8$ hydrocarbons with a boiling point range of 114° C. to 126° C. The complexed tetrahydrofuran, as well as 37.0 g of Isopar-E, is removed by distillation at 125° C. to 132.6° C. during 80 minutes. The remainder of the mixture is cooled to 22° C., and another 37.0 g Isopar-E is added to the mixture, dissolving the tris(pentafluorophenyl)borane. The yield of free tris(pentafluorophenyl)borane is 97%, with 79 ppm tetrahydrofuran remaining, as determined by NMR.

EXAMPLE 2

9 g (0.0176 mol) of tris(pentafluorophenyl)borane in 351 g of Isopar-E is transferred to a pressurizable reactor under nitrogen. Isopar-E is a product of Exxon, which is a mixture of paraffinic $C_8$ hydrocarbons with a boiling point range of 114° C. to 126° C. 1.4 g (0.0194 mol) of dry tetrahydrofuran in 20.6 g of Isopar-E is added to the solution in the reactor to make the tris(pentafluorophenyl)boranetetrahydrofuran complex to form a 2.7 wt. % solution of the complex. The complex is observed as a solid at room temperature; as the solution is heated, the complex dissolves. The temperature is raised to 160° C., and the pressure is raised to 19 psig. The tetrahydrofuran as well as the Isopar-E is distilled, and is removed via a continuous feed outlet. Isopar-E is added via a continuous feed inlet during the distillation, such that a constant volume is maintained. The distillation is conducted during 4 hours at these conditions; a total of two times the original volume of Isopar-E is added. The yield of free tris(pentafluorophenyl)borane is at least 60%, with no tetrahydrofuran detected by $^1$H NMR.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for removal of tetrahydrofuran from a tris(aryl)borane.tetrahydrofuran complex wherein said complex consists essentially of a tris(aryl)borane bound to tetrahydrofuran, which process comprises nonazeotropically distilling tetrahydrofuran at a temperature in the range of from about 115° C. to about 160° C. from a mixture comprising a tris(aryl)borane.tetrahydrofuran complex and an inert liquid hydrocarbon solvent composition.

2. A process according to claim 1 wherein the aryl groups in the tris(aryl)boranetetrahydrofuran complex are perfluoroaryl groups.

3. A process according to claim 2 wherein the aryl groups in the tris(aryl)boranetetrahydrofuran complex are pentafluorophenyl groups.

4. A process according to claim 1 wherein said liquid hydrocarbon solvent composition is boiling during the tetrahydrofuran distillation.

5. A process according to claim 1 wherein said distilling of tetrahydrofuran is conducted at a pressure in the range of from about 0 psig to about 40 psig.

6. A process according to claim 1 wherein the distillation is conducted at a pressure in the range of from about 0.5 psig to about 40 psig when said hydrocarbon solvent composition has a boiling point of less than about 115° C.

7. A process according to claim 1 wherein the distillation is conducted at a temperature of at least about 120° C.

8. A process according to claim 7 wherein the distillation is conducted at a temperature in the range of from about 120° C. to about 140° C.

9. A process according to claim 1 wherein said hydrocarbon solvent composition is comprised predominately of saturated hydrocarbons.

10. A process according to claim 9 wherein said hydrocarbon solvent composition is a mixture of paraffinic $C_8$ hydrocarbons with a boiling point range of 114° C. to 126° C.

11. A process according to claim 1 wherein said hydrocarbon solvent composition is comprised predominately of aromatic hydrocarbons.

12. A process according to claim 11 wherein said hydrocarbon solvent composition is predominately toluene.

13. A process according to claim 1 wherein the amount of tris(aryl)borane.tetrahydrofuran complex in said mixture prior to distilling is up to about fifteen weight percent.

14. A process according to claim 1 wherein additional hydrocarbon solvent composition is added during said distillation.

15. A process according to claim 1 wherein the aryl groups in the tris(aryl)boranetetrahydrofuran complex are pentafluorophenyl groups, and wherein the hydrocarbon solvent composition is a mixture of paraffinic $C_8$ hydrocarbons with a boiling point range of 114° C. to 126° C.

16. A process according to claim 1 wherein the perfluoroaryl groups in the tris(aryl)boranetetrahydrofuran complex are pentafluorophenyl groups, wherein the hydrocarbon solvent composition is predominately toluene, and wherein the pressure is in the range of from about 0.5 psig to about 40 psig.

17. A process for removal of tetrahydrofuran from a tris(aryl)borane.tetrahydrofuran complex wherein said complex consists essentially of a tris(aryl)borane bound to tetrahydrofuran, which process comprises nonazeotropically distilling, in a distillation system, tetrahydrofuran and inert liquid hydrocarbon at a temperature in the range of from about 115° C. to about 160° C. from a mixture comprising a tris(aryl)borane.tetrahydrofuran complex and an inert liquid hydrocarbon solvent composition, while continuously removing tetrahydrofuran and inert liquid hydrocarbon from the distillation system and continuously adding inert liquid hydrocarbon solvent composition to the distillation system to replace distillate removed therefrom.

18. A process according to claim 17 wherein said process is conducted such that a constant volume of distilling liquid is maintained in said distillation system.

19. A process according to claim 17 wherein the aryl groups in the tris(aryl)borane.tetrahydrofuran complex are pentafluorophenyl groups.

20. A process according to claim 17 wherein the distillation is conducted at a pressure in the range of from about 0.5 psig to about 40 psig.

21. A process according to claim 17 wherein the distillation is conducted at a temperature in the range of from about 120° C. to about 140° C.

22. A process according to claim 17 wherein said hydrocarbon solvent composition is comprised predominately of saturated hydrocarbons.

23. A process according to claim 17 wherein the aryl groups in the tris(aryl)borane.tetrahydrofuran complex are pentafluorophenyl groups, and wherein the hydrocarbon solvent composition is a mixture of paraffinic $C_8$ hydrocarbons with a boiling point range of 114° C. to 126° C.

* * * * *